United States Patent

Schweisfurth

[11] Patent Number: 5,741,219
[45] Date of Patent: Apr. 21, 1998

[54] ROLLING MASSAGE DEVICE WITH PAIRS OF TEETH

[76] Inventor: Günter Schweisfurth, Am Glaskopf 76, 57567 Daaden, Germany

[21] Appl. No.: 328,680

[22] Filed: Oct. 25, 1994

[30] Foreign Application Priority Data

Oct. 28, 1993 [EP] European Pat. Off. .............. 93117467
Dec. 23, 1993 [EP] European Pat. Off. .............. 93120695

[51] Int. Cl.$^6$ .................................................. A61H 15/00
[52] U.S. Cl. .......................... 601/119; 601/123; 601/125; 601/135
[58] Field of Search ............................ 601/119, 122–129, 601/118, 115, 141, 135

[56] References Cited

U.S. PATENT DOCUMENTS

| | | | |
|---|---|---|---|
| 1,630,149 | 5/1927 | Wahrt | 601/119 |
| 3,662,748 | 5/1972 | Thurman . | |
| 4,067,324 | 1/1978 | Greenawalt | 601/120 |
| 4,993,408 | 2/1991 | Schweisfurth | 601/123 |

FOREIGN PATENT DOCUMENTS

| | | | |
|---|---|---|---|
| 465348 | 1/1992 | European Pat. Off. | 601/125 |
| 668225 | 10/1929 | France . | |
| 1081487 | 12/1954 | France | 601/120 |
| 497146 | 5/1930 | Germany . | |
| 123232 | 11/1927 | Switzerland . | |
| 1718928 | 3/1992 | U.S.S.R. | 601/119 |
| 87/01031 | 2/1987 | WIPO . | |

OTHER PUBLICATIONS

Rimpler, M. : Dermapunktur—Eine Neue Möglichkeit Zur Schmerzbehandlung Biologische Medizin 6, 370–373 (1990).

Klein, J., Blarr, A.: Therapie Chronischer Schmerzen on Der Orthopädie Mit Der Dermapunktur. Biologische Medizin 6, 823–828 (1991).

Rimpler, M.: Dermapunktur—Eine Neue Methode Zur Gezielten Schmerzbehandlung. Physikaliche Medizin 3, 61–64 (1993).

Rimpler, M.: Die Dermapunktur–Fibel. ISBN 3-924191-65-4 Günter Albert Ulmer Verlag, Tuningen (1993).

Rimpler, M.: Schmerztherapie Mit Hautroller. Münchner Medizinische Wochenschrift 20, 13 (1994).

Doering, TH. J., Gehrke TH., Rimpler, M., Gehrke, A.: Veränderungen Des Cerebralenblutflusses Während Der Dermapunktur–Rollung.

Primary Examiner—Danton D. DeMille
Attorney, Agent, or Firm—Friedrich Kueffner

[57] ABSTRACT

A rolling massage device for massaging skin areas and reflex zones of the human body includes at least one shaft mounted on a handle and massage rings or rolling bodies which are freely rotatably mounted on the shaft. The massage rings or rolling bodies have prong-like, tooth-like, or needle-like projections which are preferably uniformly distributed in circumferential direction. The massage rings or rolling bodies are spaced apart from each other by means of spacer rings which are also mounted on the shaft. Each massage ring or rolling body is provided with a double row or multiple rows of projections. The rows of projections have a predetermined or fixed lateral spacing between each other. The projections of adjacent rows of projections are arranged staggered relative to each other in circumferential direction.

17 Claims, 5 Drawing Sheets

FIG.4
FIG.5
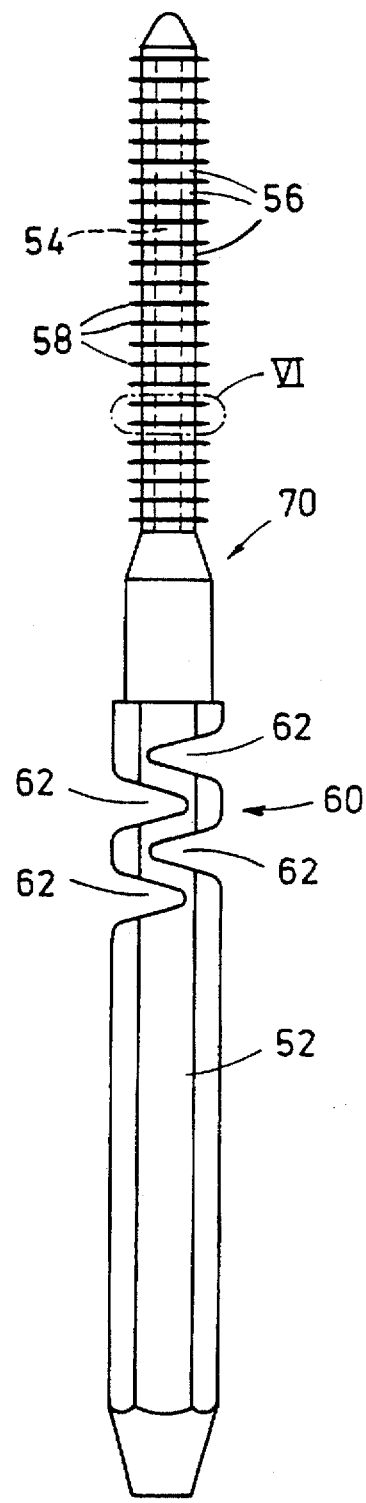
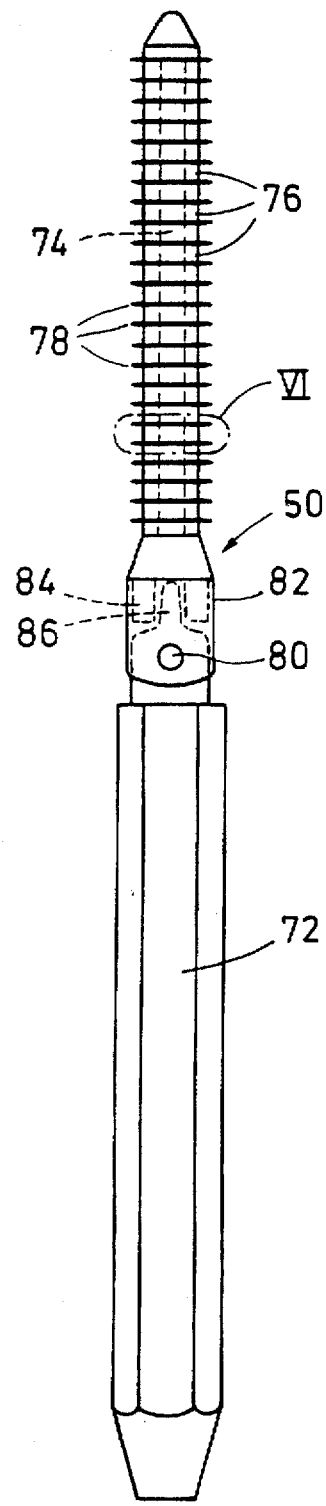

ROLLING MASSAGE DEVICE WITH PAIRS OF TEETH

BACKGROUND OF THE INVENTION

1. Field of the Invention

The present invention relates to a rolling massage device for massaging skin areas and reflex zones of the human body. The rolling massage device includes at least one shaft mounted on a handle and massage rings or rolling bodies which are freely rotatably mounted on the shaft. The massage rings or rolling bodies have prong-like, tooth-like, or needle-like projections which are preferably uniformly distributed in circumferential direction. The massage rings or rolling bodies are spaced apart from each other by means of spacer rings which are also mounted on the shaft.

2. Description of the Related Art

Massage devices of the above-described type are already known from EP-B1-0 142 132 and EP-A1-0 465 758. At least the rolling massage devices according to EP-B1-0 142 132 have been found very useful in practical application. These rolling massage devices produce an acupuncture-like effect without destroying the skin and, consequently, produce a point-by-point massaging effect when they are used in self-treatment for carrying out a rolling massage of skin areas and reflex zones. It is important in this connection that the skin stimulations produced by the rolling massage frequently make it possible to achieve favorable therapeutic effects if a good surface massage is carried out at aching body areas and/or the respective reflex zones.

More recent human physiological studies, particularly stimulation or sensory physiological studies, have produced the finding that the effect of the above-described rolling massage devices depends significantly on the number of stimulation points in the skin areas or reflex zones being treated. Specifically, the studies have shown that the massaging effect is improved with increasing number of simultaneously activated stimulation points. These medical results can be clearly seen in the electroencephalogram, the electromyogram and in Doppler tests.

The findings obtained in these studies have been reported, for example, in the following papers (1)–(6):

(1) Rimpler, M.: Dermapunktur—eine neue Möglichkeit zur Schmerzbehandlung [Dermapuncture—A New Possibility of Pain Treatment]. Biologische Medizin 6, 370–373 (1990)

(2) Klein, J., Blarr, A.: Therapie chronischer Schmerzen in der Orthopädie mit der Dermapunktur [Therapy of Chronic Pain in Orthopedics with Dermapuncture]. Biologische Medizin 6, 823–828 (1991)

(3) Rimpler, M.: Dermapunktur—eine neue Methode zur gezielten Schmerzbehandlung [Dermapuncture—A New Method of Specific Pain Treatment]. Physikaliche Medizin 3, 61–64 (1993)

(4) Rimpler, M.: Die Dermapunktur-Fibel [The Dermapucture Primer]. ISBN 3-924191-65-4 Günter Albert Ulmer Verlag, Tuningen (1993)

(5) Rimpler, M.: Schmerztherapie mit Hautroller [Pain Therapy with Skin Rollers]. Münchner Medizinische Wochenschrift 20, 13 (1994)

(6) Doering, Th. J., Gehrke Th., Rimpler, M., Gehrke, A.: Veränderungen des cerebralen Blutflusses während der Dermapunktur-Rollung [Changes of the Cerebral Blood Flow During Dermapuncture Rolling]. Bericht aus der Klinik für Physikalische Medizin und Rehabilitation, Medizinische Hochschule Hannover (1994).

The studies have produced the result that dermapuncture makes it possible to release reactions in the organism which make possible a "help through self-help" and which can be clinically utilized in a specified manner. Moreover, because of its simplicity and lack of complication, dermapuncture is particularly suitable for ambulant therapy and will soon have its fixed place in pain therapy (3).

Since these rolling massage devices should be very easy and simple to manipulate, particularly when they are used for self-treatment, the lengths of the shafts equipped with the massage rings or rolling bodies cannot be increased to a great extent in order to achieve the desired high number of simultaneously activated stimulation points on the skin areas and/or in the reflex zones of the human body.

SUMMARY OF THE INVENTION

Therefore, it is the object of the present invention to provide a rolling massage device of the above-described type which takes into account the above-described findings in an optimum manner. Specifically, it is the object of the invention to provide a possibility of substantially increasing the number of activatable stimulation points on the skin or in the reflex zones of the human body, without requiring an increase of the length of the shafts of the rolling massage device which support the massage rings or rolling bodies.

In accordance with the present invention, the above object is met by a rolling massage device which has the following features:

- each massage ring or rolling body is provided with a double row or multiple rows of projections;
- the rows of projections have a predetermined or fixed lateral spacing between each other; and
- the projections of adjacent rows of projections are arranged staggered relative to each other in circumferential direction.

If the lateral distance between adjacent rows of projections can be selected so small that it corresponds at least approximately to half the spacing between projections arranged successively in circumferential direction within one row of projection, it is advantageous if the distance by which the projections of adjacent rows of projections are staggered relative to each other in circumferential direction is also equal to half the spacing between projections within one row of projections.

In accordance with a particularly advantageous feature of the present invention, the massage rings or rolling bodies are constructed as toothed wheels with a double row or multiple rows of teeth, wherein each row has a plurality of teeth which have a conically outwardly narrowing shape. The free ends of these teeth should have a convexly arched crest, so that undesirable injury to the skin is prevented.

In accordance with another feature, two disk members constructed as flat bevel wheels and arranged mirror-inverted relative to each other in cross section can be fixedly connected to each other to form a wheel with a double row of teeth. The teeth may be arranged in such a way that the outer side surfaces of all teeth are in alignment with the outer surface of the disk member, while the inner surfaces of all teeth are inclined away from the common center plane of the two disk members.

The two disk members can be connected to each other by means of pressing, welding, riveting or gluing to form the double-row wheel. The disk members may be composed of metal or plastics material.

The two disk members can be connected in a particularly simple and advantageous manner into a double-row wheel by providing one of the two wheel members with an axially projecting collar which surrounds the center hole of the disk member, wherein this collar can be inserted into the center hole of the other disk member, and wherein the rim of the neck protrudes slightly beyond the outer side of the other disk member and is bent toward the edge of the center hole of the other disk member.

If, in that case, the edge of the other disk member is unilaterally chamfered, this chamfered portion can form a receiving means for the bent rim of the neck of the first disk member, so that this bent rim does not project or projects only insignificantly beyond the outer side surface of the other disk member.

The bent rim at the collar of the first disk member can be most easily produced by pressing, while the collar of the disk member itself is obtained by a deep drawing process.

In accordance with another feature, the collar of the one disk member projects away from that side surface of the disk member at which the side surfaces of the teeth are inclined.

Each of the disk members forming a flat bevel wheel advantageously may have a thickness of 0.8 mm. As a result, massage rings or rolling bodies having a total thickness of only 1.6 mm are available.

It has been found that the therapeutic effect is advantageously influenced if the crests at the free ends of the teeth are arched in the direction of the plane of the disk member with a radius of 0.25 mm, while the crests are arched with only a radius of 0.15 mm in a direction transversely of the disk member plane.

It is also within the scope of the present invention to manufacture the toothed wheels forming the massage rings or rolling bodies with a double row or multiple rows of projections as single-piece diecast or injection molded members of metal or plastics material. However, the manufacture of the massage rings or rolling bodies is simpler if individually punched-out disk members which are deformed into flat bevel wheels are connected by pressing, welding, riveting or gluing in such a way that the projections thereof are placed in a position in which the projections of the two disk members are staggered relative to each other in circumferential direction.

The rolling massage devices equipped with massage rings or rolling bodies in accordance with the present invention can be constructed with respect to their basic structure as described in EP-B1-0 143 132 and EP-A1-0 465 758. However, additional proposals for constructing the device in accordance with the older German patent application P 43 12 326 may also be utilized.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

BRIEF DESCRIPTION OF THE DRAWING

In the drawing:

FIG. 4 is a side view of another embodiment of the massage device of the present invention;

FIG. 5 is a side view of yet another embodiment of the rolling massage device;

DETAILED DESCRIPTION OF THE PREFERRED EMBODIMENTS

Figure 6:
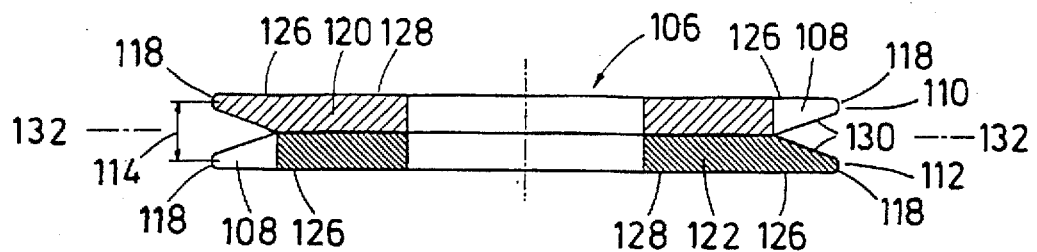
FIG. 6 is a sectional view, on a substantially larger scale, showing a detail of the rolling massage device indicated by VI in FIGS. 1–5.
Figure 7:
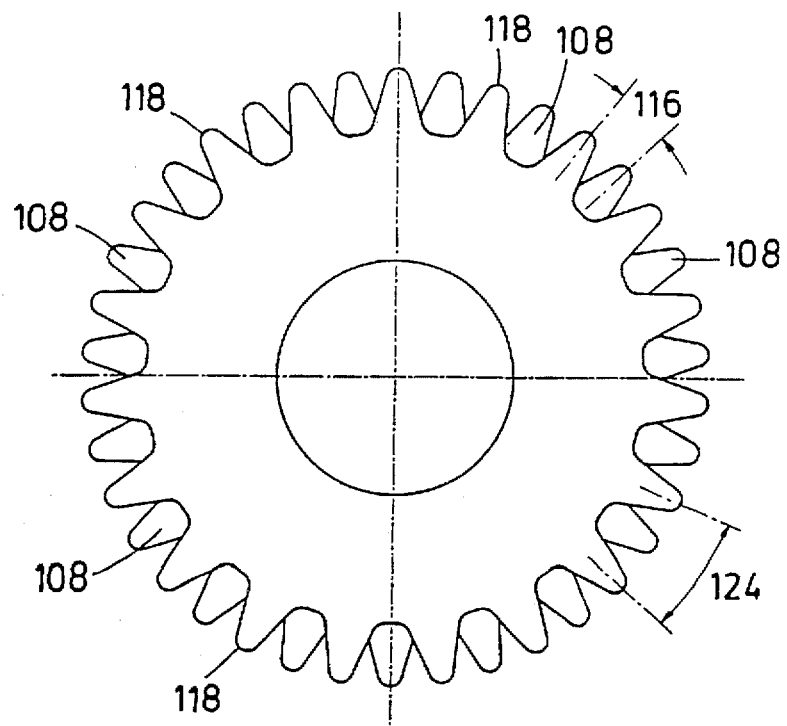
FIG. 7 is a side view of the detail of FIG. 6.
Figure 8:
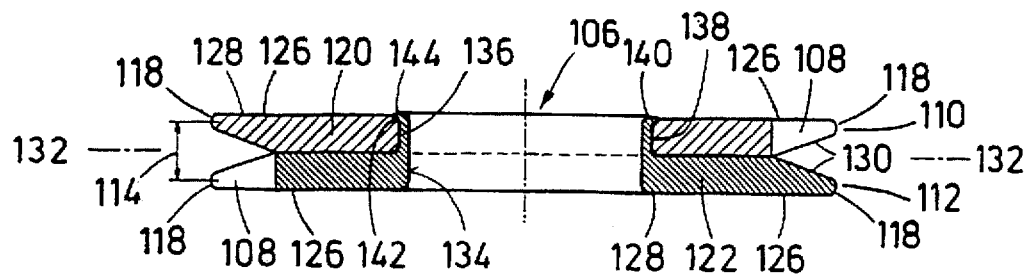
FIG. 8 is a sectional view, again on a substantially larger scale, showing a further development of the detail illustrated in FIG. 6.

The rolling massage devices described in detail below with the aid of FIGS. 1–5 and 10 are merely preferred embodiments and the use of the specific configurations of the massage rings or rolling bodies described with the aid of FIGS. 6 to 8 is not limited to these embodiments. Rather, the massage rings or rolling bodies shown in FIGS. 6 to 8 can also be used in other embodiments of rolling massage devices, particularly in those described in the aforementioned EP-B1-0 142 132 and EP-1-A1-0 465 758.

Figure 1:
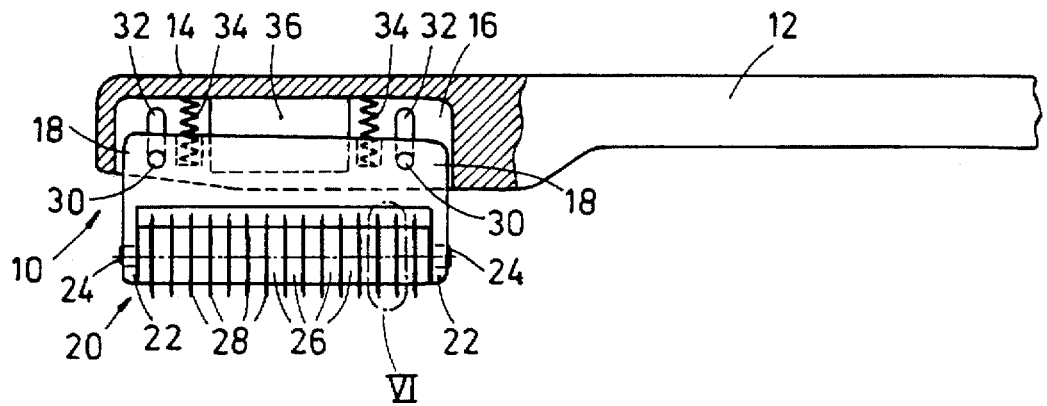
FIG. 1 is a side view, partially in section, of a first embodiment of the rolling massage device according to the present invention.

FIG. 1 of the drawing shows a rolling massage device 10 which includes a handle 12 whose front end 14 has an increased thickness or raised configuration. A pocket 16 which is open toward one longitudinal side is formed in the increased thickness or raised end 14. A fork-shaped member 20 is guided with a block-like rear portion 18 in the pocket 16. The two sides 22 of the fork-shaped member 20 support a shaft 24. A large number of massage rings or rolling bodies 26 are freely rotatably mounted on the shaft 24. Each of the massage rings or rolling bodies 26 has a plurality of projections 28 which form needle pins or teeth and are arranged uniformly distributed over the circumference of the massage rings or rolling bodies 26. At least each of the projections 28 of the massage rings or rolling bodies constructed as a needle pin or tooth is provided with a coating of noble metal, for example, silver or gold.

The massage rings or rolling bodies 28 are kept at a distance from each other by means of spacer rings 26. The spacer rings 26 are mounted freely rotatably on the shaft 24. However, it is also possible to attach each spacer ring to one of the two adjacent massage rings or to form each spacer ring as a single piece with one of the two adjacent massage rings.

A significant structural feature of the rolling massage device 1 shown in FIG. 1 is that the block-like rear portion 18 of the fork-shaped member 20 is received by the pocket 16 of the handle 12 in such a way that the rear portion 18 can be displaced to a limited extent in the pocket 16 of the handle 12 only parallel to its principal plane and essentially transversely of the shaft 24. For this purpose, in the embodiment of FIG. 1, the fork-shaped member 20 interacts with the front end 14 of the handle 12 through bolts 30 which extend through oblong holes 32 in transverse direction. In accordance with FIG. 1, the bolts 30 are inserted in holes of the block-like rear portion 18 and interact with oblong holes 32 provided in side walls of the front end 14 which define the pocket 16. Of course, the reverse arrangement of bolts 30 and oblong holes 32 is also possible.

In the rolling massage device 10 shown in FIG. 1, the fork-shaped member 20 interacts with the front end 14 of the handle 12 through two bolts 30 and corresponding oblong holes 32. It would also be conceivable instead to provide only one bolt 30 with a corresponding oblong hole 32 and to arrange these operational elements at half the length of the fork-shaped member 20 and the pocket 16.

Another significant structural feature of the rolling massage device 10 of FIG. 1 is that the shaft 24 supporting the massage rings or rolling bodies 26 is held in the handle 12 through a support connection which is at least to a limited extent elastically yielding or resilient in a direction extending transversely of the longitudinal direction thereof. In order to form this elastically yielding support connection, it is possible to mount a plurality of helical compression springs 34 between the block-like rear portion 18 of the fork-shaped member 20 and the bottom of the pocket 16 at the front end 14 of the handle 12. In the embodiment shown in FIG. 1, for example, two helical compression springs 34 are provided near the support connection formed by bolts 30 and oblong holes 32. In accordance with an advantageous feature, the helical compression springs 34 are received in blind-end holes which are open at the rearward end surface of the block-like rear portion 18.

By releasing the support connection formed by bolts 30 and oblong holes 32, it is possible to expose the helical compression springs 34 and to replace them with other helical compression springs having a different spring force if it is desired to vary the intensity of the elastically yielding connection.

In order to form the connection which is elastically yielding to a limited extent it is also possible to use an elastomer block 36 instead of or in addition to the helical compression springs 34. This elastomer block 36 is also mounted between the block-like rear portion 18 of the fork-shaped member 20 and the bottom of the pocket 16 in the front end 14 of the handle 12. The elastomer block 36 may also be partially received in a recess which is open toward the rearward end face of the block-like rear portion 18. The material of the elastomer block 36 may be foamed rubber or a similar material which can be compressed without significantly increasing its restoring force.

Figure 2:
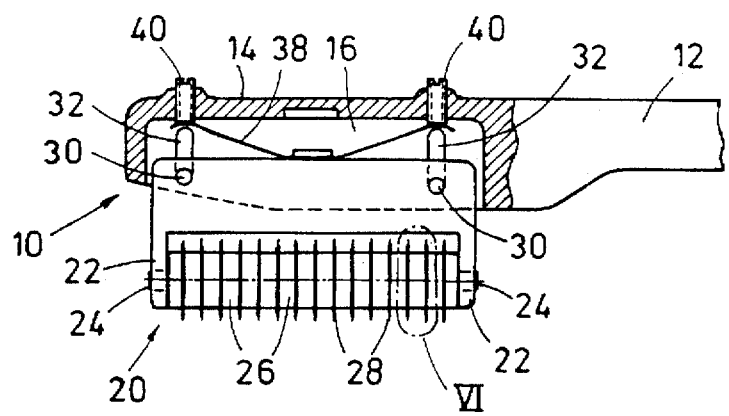
FIG. 2 is a side view, partially in section, of a second embodiment of the massage device according to the present invention.

FIG. 2 of the drawing shows a rolling massage device 10 which is essentially of the same construction as the rolling massage device 10 shown in FIG. 1. The only difference is that, instead of the helical compression springs 34 or the elastomer block 36 for forming the connection which is elastically yielding at least to a limited extent, a leaf spring stirrup 38 is used which is placed in the pocket 16 and rests against the bottom of the pocket 16, on the one hand, and against the rearward end face of the block-like rear portion 18, on the other hand. The use of leaf spring stirrups 38 as elastically yielding support elements is particularly recommended if it is desired to vary the elastic behavior. This is because it is possible in this case that adjusting screws 40 are provided in the bottom of the pocket 36 for influencing the elastic pretension of the leaf spring stirrups 38.

Figure 3:
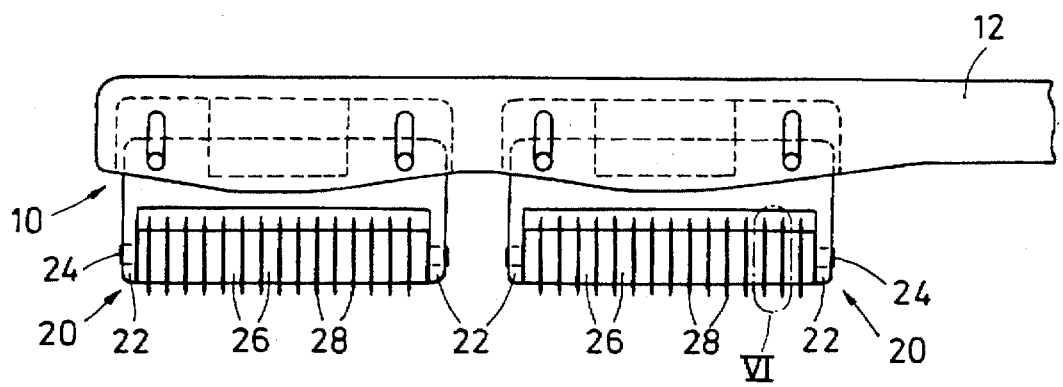
FIG. 3 is a side view of a further development of the rolling massage devices of FIGS. 1 and 2.

In the rolling massage devices 10 shown in FIGS. 1 and 2, each handle 12 is equipped with only one fork-shaped member 20 which carries the shaft 24 with the massage rings or rolling bodies 26. FIG. 3, on the other hand, shows an embodiment of the rolling massage device 10 in which the handle 12 is equipped with two fork-shaped members 20 each of which has a shaft 24 supporting the massage rings or rolling bodies 26 with the projections 28 constructed as needle pins, wherein the shafts 24 are mounted between the sides 22 of the two fork-shaped members 20.

In the embodiment of FIG. 3, each of the two fork-shaped members 20 is individually connected to the handle 12 in the same manner which is elastically yielding to a limited extent, as is the case in the embodiments of FIGS. 1 and 2.

The interaction of the fork-shaped members 20 with the handle 12 can also be achieved in a manner which differs from that shown in FIGS. 1 and 2. Thus, the support connections formed by the bolts 30 and the oblong holes 32 can be replaced by providing cap bolts which extend in the front end 14 of the handle 12 through holes in the bottom of the pocket 16 and which are anchored in the block-like rear portion 18 of the fork-shaped member 20. These cap bolts can be arranged, for example, in axial alignment with the helical compression spring 34.

On the other hand, it is also possible to glue the elastomer block 36 to the bottom of the pocket 16, on the one hand, and to the fork shaped member 20, on the other hand, in order to obtain an undetachable but elastically yielding support connection of the fork shaped member 20 with the handle 12.

FIG. 4 of the drawing shows an embodiment of the rolling massage device 50 according to the present invention which is provided with a rod-shaped handle 52 which supports a shaft 54 on which are mounted a plurality of freely rotatably supported massage rings or rolling bodies 56. Each of the massage rings or rolling bodies 56 is provided with projections 58 in the form of needle pins which are uniformly distributed over the circumference of the massage ring or rolling body 56, wherein at least the needle pins have a surface coating of noble metal, such as silver or gold. The massage rings or rolling bodies 58 are kept at a distance from one another by means of spacer rings 56.

The significant feature of the rolling massage device 50 of FIG. 4 is that the connecting portion 60 between the handle 53 and the shaft 54 supporting the massage rings or rolling bodies 56 has a bending-elastic configuration.

The bending-elastic configuration can be achieved, for example, by constructing the connecting portion 60 of an elastomer portion and/or of bending rod springs.

However, FIG. 4 of the drawing shows an embodiment in which the connecting portion 60 between the handle 52 and the shaft 53 is provided with transverse indentations 62 which are arranged on alternating sides and offset relative to each other in longitudinal direction. The transverse indentations 62 diverge from the inside toward the outside in the shape of a wedge or V and define over the connecting portion 60 a zig-zag shaped or wave-shaped shaft portion having a substantially reduced effective cross section. This provides the handle 52 through the connecting portion 60 with a certain bending elasticity, even if the material, particularly plastics material, used for manufacturing the handle 52 is in itself relatively rigid. The elastically yielding behavior of the connecting portion 60 can be influenced as desired by an appropriate positioning and configuration of the transverse indentations 62.

The massage device 70 shown in FIG. 5 is structurally very similar to the massage device 50 of FIG. 4. The rod-shaped handle 72 of the massage device 50 supports the shaft 74 on which the massage rings or rolling bodies 76 are freely rotatably mounted, wherein each massage ring or rolling body 76 has projections 78 in the form of needle pins which are arranged uniformly distributed over the circumference of the massage ring or rolling body 76.

However, the rolling massage device 70 of FIG. 5 differs from the massage device 50 of FIG. 4 in that the shaft 74 is connected to the handle 72 through a transverse joint 80. This transverse joint 80 provides the shaft 74 with a certain angular mobility relative to the handle 72. This angular mobility is used in the present case for obtaining between the shaft 74 and the handle 72 a connection which is elastically yielding at least to a limited extent. For this purpose, on the side of the transverse joint 80 facing the shaft 74, a tubular elastomer body 84 is received in a sleeve member 82, wherein a tongue 86 projecting from the handle 72 engages in the tubular elastomer body 84.

The elasticity inherent in the elastomer body 84 determines the extent of the angular displacement of the shaft 74 about the transverse joint 80 relative to the handle 72 when a pressure is exerted from the handle 72 on the shaft 74 supporting the massage rings or rolling bodies 76.

In all of the rolling massage devices 10, 50 and 70 described above in detail, and also in the rolling massage devices of known construction merely mentioned above, massage rings or rolling bodies 106 as shown in FIGS. 6 and 7 can be used with particular advantage. The massage rings or rolling bodies 106 according to FIGS. 6 and 7 are also provided with a plurality of projections 108 which are uniformly distributed over the circumference. However, these projections 108 do not have the shape of a true needle tip; rather, the projections 108 have a shape which narrows toward the free end in the manner of a tooth or prong.

The particular feature of the massage rings or rolling bodies 106 according to FIGS. 6 and 7 is the fact that the projections 108 are arranged in at least two rows 110 and 112 parallel to each other, i.e., they form a double row 110/112.

Of course, a massage ring or rolling body 106 may also be equipped with more than two rows 110, 112 of projections 103 and, consequently, may be provided with multiple rows of projections.

As clearly indicated in FIG. 6 of the drawing, the adjacent parallel rows 110 and 112 of projections 108 have a predetermined or fixed lateral distance 114 therebetween. Moreover, the projections 108 in the adjacent rows 110 and 112 are arranged so as to be staggered relative to each other, as indicated by reference numeral 116 in FIG. 7.

It can be concluded from FIGS. 6 and 7 of the drawing that the massage rings or rolling bodies 106 are constructed as toothed wheels with a double row or multiple rows of teeth, wherein each row 110 and 112 has a plurality of projections 108 in the form of outwardly conically narrowing teeth, wherein the free ends of the teeth are provided with a convexly arched crest 118.

As also shown in FIG. 6 of the drawing, in a preferred embodiment of the massage rings or rolling bodies 106, two disk members 120 and 122 constructed as flat bevel wheels are arranged in a mirror-inverted manner with respect to their cross section. These disk members 120 and 122 are of equal construction and are preferably manufactured by punching out and compression molding from relatively thin sheet metal. The two disk members 120 and 122 can be connected to each other to form a double toothed wheel by means of pressing, welding or gluing. Preferably, the distance 116 by which the projections 108 of the two disk members 120 and 122 are staggered relative to each other in circumferential direction corresponds to half the spacing 124 between successive projections 108 in each disk member 120 and 122.

FIG. 6 further shows that the two disk members 120 and 122 constructed separately as flat bevel wheels are combined to form a massage ring or rolling member 106 in such a way that the outer side surface 126 of each tooth or projection 108 is in alignment with the outer surface 128 of the disk members 120 and 122, while the inner side surface 130 of each tooth or projection 108 is inclined away from the common center plane 132—132 of the two disk members 120 and 122.

It has been advantageous in practical use if the crests 118 at the free ends of the teeth or projections 108 are arched in the direction of the principal plane of the disk members 120 and 122 with a radius of 0.25 mm, while the crests 118 should have a radius of only 0.15 mm in the direction transversely of the disk member plane. It has also been found useful to use disk members 120, 122 which have a thickness of 0.8 mm, so that the total thickness of each massage ring or rolling body 106 is 1.6 mm. Consequently, the lateral distance 114 between the centers of the teeth or projections 108 of two parallel rolls 110 and 112 is approximately 1.3 mm.

The outer diameter of an embodiment of the massage rings or rolling bodies which is in use may be approximately 13.5 mm, so that the circumference is 42.39 mm. Nineteen teeth are uniformly distributed over this circumference. Consequently, a massage ring or rolling body 106 equipped with a double row of projections 108 has 38 teeth or projections 108 whose convexly arched crests 118 form skin stimulation points. The lateral distance 114 between skin stimulation points is approximately 1.3 mm and the spacing between skin stimulation points in rolling direction of the massage rings or rolling bodies 106 is approximately 1.12 mm.

It should be pointed out that the disk members 120 and 122 can also be manufactured from a suitable plastics material, wherein subsequently two disk members 120 and 122 are connected to form a massage ring or rolling body 106 with two rows of teeth by pressing, welding, riveting or gluing the disk members together.

However, it is also conceivable to manufacture the toothed wheels forming the massage rings or rolling bodies 106 with the projections 108 arranged in double rows or multiple rows as single-piece diecast or injection molded parts of metal or plastics material.

Moreover, it is also possible to form each individual disk member 120, 122 as a flat double bevel wheel to form a double toothed wheel. In that case, the outer side surfaces 126 as well as the inner side surfaces 130 of each disk member 120, 122 are inclined relative to the outer side 128 or the common center plane 132—132, respectively. The lateral distance 114 between adjacent rows 110 and 112 of projections 108 is then reduced to 0.8 mm, while all other dimensions remain the same.

The massage rings or rolling bodies 106 of the type described last can be freely rotatably mounted next to each other on the shaft attached to the handle without the use of spacer rings, while still ensuring that the lateral distance 114 is also maintained between the crests 118 of the projections 108 of adjacent massage rings or rolling bodies 106.

Of course, the drawing and the above description merely relate to examples of the rolling massage device according to the present invention. In other words, the present invention is not limited to these examples. Rather, the scope of the invention includes all rolling massage devices of the above-described type as long as the massage rings or rolling bodies 26, 56, 76 have the configuration described above in detail with the aid of FIGS. 6 and 7.

In order to be complete, it is additionally pointed out that at least the projections 108 of the massage rings or rolling bodies 106 shown in FIGS. 6 and 7 can be provided with a coating of noble metal, for example, silver or gold.

Figure 9:
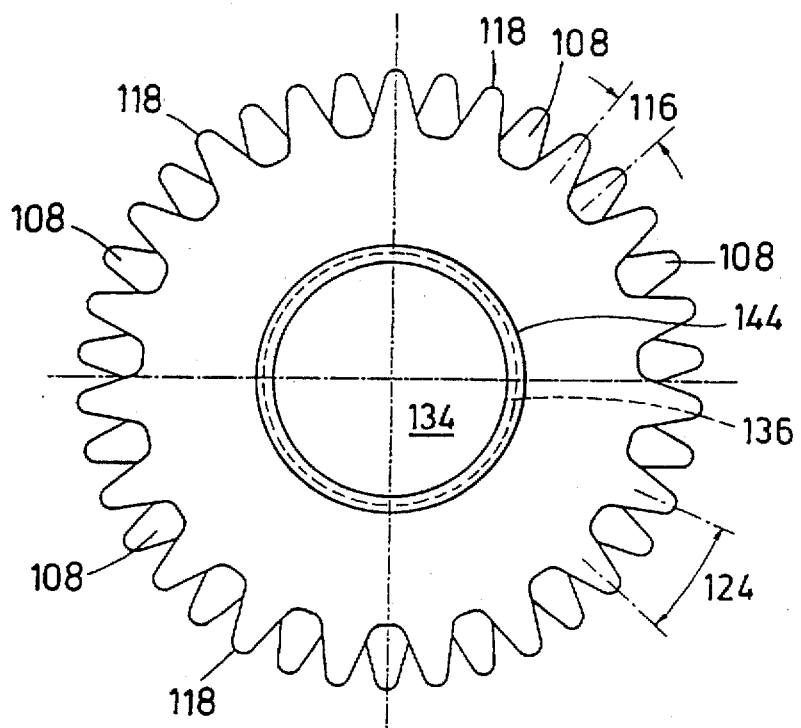
FIG. 9 is a side view of the detail of FIG. 8.

The massage rings or rolling bodies 106 shown in FIGS. 8 and 9 are constructed in the same manner as FIGS. 6 and 7 of the drawing as double toothed wheels which are formed by two disk members 120 and 122 which are prefabricated as flat bevel wheels.

However, contrary to the embodiment of FIGS. 6 and 7, the disk members 120 and 122 of FIGS. 8 and 9 are not of equal construction. While they are again manufactured by punching out and compression molding from relatively thin sheet metal, the disk members of FIGS. 8 and 9 are of different basic construction. Thus, the disk member 122 is provided with a unilaterally protruding collar 136 which surrounds the center hole 34 of the disk member 122. When the disk member 122 is manufactured of thin sheet metal, the collar 136 can advantageously be produced by a deep drawing process. In this case, the collar 136 is formed in such a way that it protrudes beyond that side surface of the disk member 122 at which the inner side surfaces 130 of the teeth or projections 108 are inclined away from the common center plane 132—132 of the two disk members 120 and 122.

The collar 136 is preferably formed by the deep drawing process in such a way that it has a wall thickness which is as small as possible while still being sufficiently stable. The length of the collar 136 should be dimensioned in such a way that it is only slightly greater than the thickness of the other disk member 120.

The diameter of the center hole 138 in the disk member 120 is greater than the diameter of the corresponding center hole 134 in the disk member 122. The center hole 138 of the disk member 120 corresponds with as little play as possible to the outer diameter of the collar 136, so that the collar 136 can be inserted into the center hole 138. After the collar 136 has been inserted in the center hole 138, the free rim 140 of the collar 136 projects slightly beyond the outer side surface 126 of the disk member 120 and can be bent at the outer side surface 126 against the edge of the center hole 138.

It has been found advantageous if the edge of the center hole 138 in the disk member 120 has a chamfered portion 142 at the outer side surface 126, wherein the chamfered portion 142 receives the bent rim 144 of the collar 136, so that the collar 136 does not project or only slightly projects beyond the outer side surface 126 of the disk member 120. In the simplest case, the bent rim 144 can be formed by pressing, wherein for manufacturing the bent rim a pressing force is used which ensures that the two disk members 120 and 122 are fixed relative to each other so that they rotate together.

It is readily apparent that, contrary to FIGS. 6 and 8, it is also possible to combine more than two disk members to a massage ring or rolling body 106 or to a toothed wheel with a plurality of teeth, if this is desired or required.

The connection can also in this case be obtained by pressing, welding, riveting or gluing.

However, similar to the embodiment of FIG. 8, the disk member 122 may have a collar 136 which is sufficiently long so as to make it possible to place several disk members 120 of the other type onto the collar 136 before the rim 140 of the collar 136 is being bent. Each additional disk member mounted between the disk members 120 and 122 is advantageously provided in the area of the projections 108 with oppositely inclined side surfaces, so that the lateral distance 114 between the crests 118 of all projections 108 is maintained.

Figure 10:
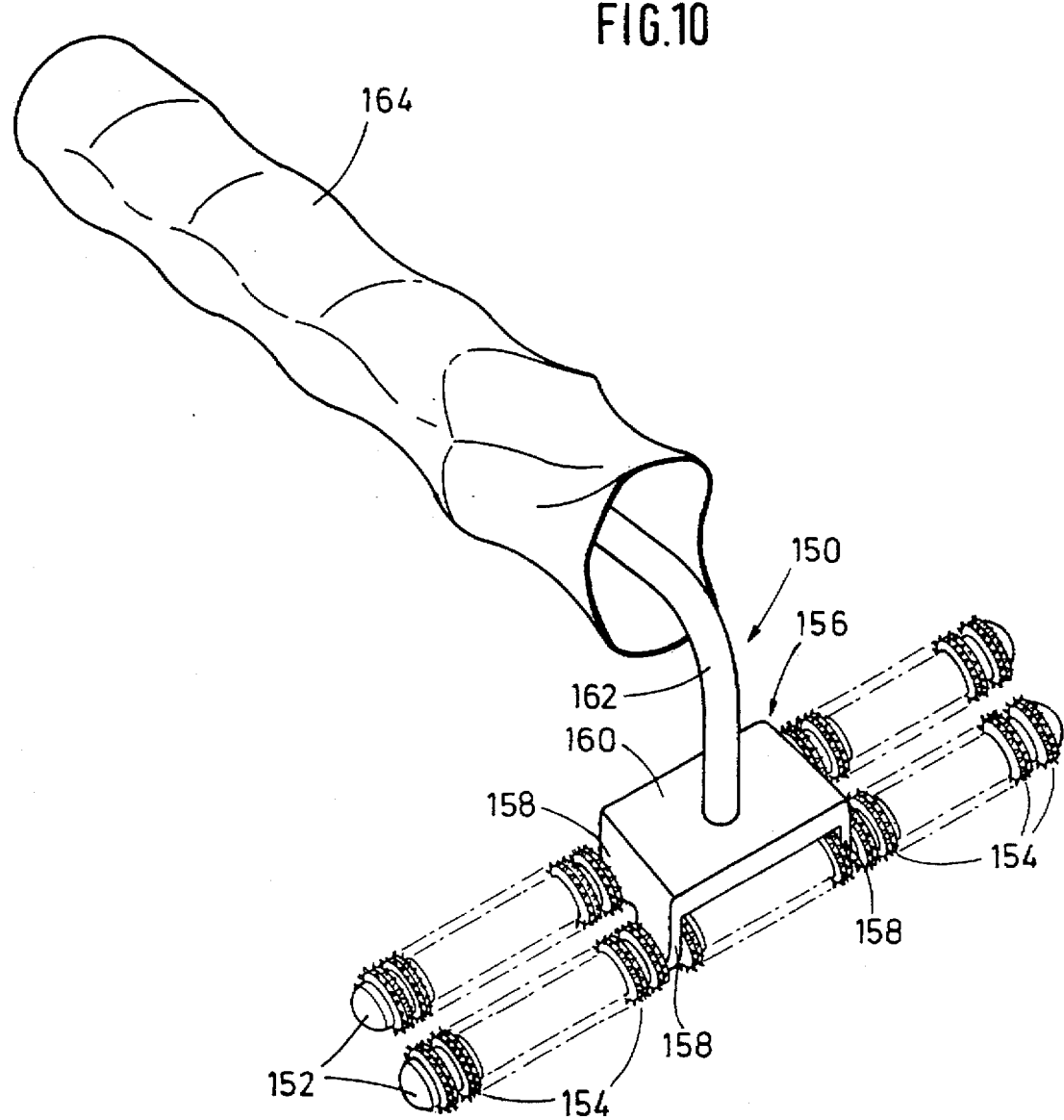
FIG. 10 is a perspective front view of a final embodiment of the rolling massage device according to the present invention.

In order to be complete, FIG. 10 shows a massage device 150 which has two parallel shafts 152, wherein massage rings or rolling bodies 154 are freely rotatably mounted on the shafts 152.

The two shafts 152 are supported by a U-shaped support member 156 which is provided with flanges 158. Bearing eyes, not shown, which are in alignment with each other are arranged in the flanges 158. Each pair of bearing eyes receives one of the shafts 152.

A connecting bolt 162 is attached to and extends perpendicularly from the web 160 of the U-shaped support member 156. The other end of the connecting bolt 162 is connected to a handle 164. The connecting bolt 162 and the handle 164 include an angle of 120° with each other.

As illustrated in FIG. 10, the massage rings or rolling bodies 154 are constructed as already described in connection with FIGS. 6–9. Accordingly, each massage ring or rolling body 154 has a double row of projections 108, wherein the rows of projections have a predetermined or fixed lateral distance 114 between each other and the projections of adjacent rows are arranged staggered relative to each other in circumferential direction.

The massage device 150 shown in FIG. 10 is particularly suitable for carrying out a treatment of a person by another person because it is constructed in such a way that, for example, a masseur can carry out a treatment of a person who is lying down, wherein the masseur can apply pressure against the body portions to be treated.

The invention is not limited by the embodiments described above which are presented as examples only but can be modified in various ways within the scope of protection defined by the appended patent claims.

I claim:

1. A massage device for carrying out a rolling massage of skin areas and reflex zones of the human body, the massage device comprising a handle, at least one shaft attached to the handle, a plurality of ring-shaped rolling bodies mounted on the at least one shaft, each rolling body having a plurality of projections uniformly distributed in a circumferential direction thereof, the projections being arranged in two rows, wherein the projections within one row of projections are spaced apart from each other by a division distance, wherein the projections of adjacent rows of projections on each rolling body are arranged staggered relative to each other in the circumferential direction, and wherein the projections of adjacent rows of projections are spaced apart from each other in circumferential direction by a stagger distance, the stagger distance corresponding to approximately half the division distance, wherein each rolling body comprises two disk members attached to each other in a mirror-inverted arrangement, each disk member having one of the rows of projections, the projections being teeth having outer and inner side surfaces, the disk members having outer surfaces and inner surfaces, the disk members being attached to each other at the inner surfaces in a common center plane, the outer side surfaces of the teeth being in alignment with the outer surfaces of the disk members, and the inner side surfaces of the teeth being inclined away from the center plane.

2. The massage device according to claim 1, further comprising spacer rings mounted on the at least one shaft for maintaining a distance between the rolling bodies.

3. The massage device according to claim 1, wherein the projections are one of tooth-like, prong-like and needle-like projections.

4. The massage device according to claim 1, wherein the projections being outwardly conically narrowing teeth, and wherein the teeth have free ends, each free end comprising a convexly arched crest.

5. The massage device according to claim 4, wherein the disk members forming the rolling bodies with the projections arranged in at least two rows are one of diecast or injection molded members of metal or plastics material.

6. The massage device according to claim 4, wherein each rolling body has a plane of rotation, the crest at the free end of each tooth having a radius of approximately 0.25 mm in a direction of the plane of rotation and a radius of approximately 0.15 mm in a plane extending transversely of the plane of rotation.

7. The massage device according to claim 1, wherein the two disk members are attached to each other by one of pressing, welding, riveting and gluing.

8. The massage device according to claim 1, wherein the disk members are of metal or plastics material.

9. The massage device according to claim 1, wherein each disk member has a thickness of 0.8 mm.

10. The massage device according to claim 1, wherein at least the projections of the rolling bodies have a coating of noble metal.

11. The massage device according to claim 10, wherein the noble metal is silver or gold.

12. The massage device according to claim 1, wherein each disk member has a center hole, a first of the two disk members having a unilaterally projecting collar surrounding the center hole thereof, the collar of the first disk member being inserted into the center hole of a second of the disk members, the center hole of the second disk member having an edge, the collar having a rim, the rim of the collar projecting beyond the outer surface of the second disk member, the rim of the collar having a bent portion in contact with the edge of the center hole of the second disk member.

13. The massage device according to claim 12, wherein the edge of the center hole of the second disk member has a chamfered portion, wherein the chamfered portion receives the bent portion of the collar.

14. The massage device according to claim 12, wherein the bent portion of the neck of the first disk member is a pressed member.

15. The massage device according to claim 12, wherein the collar of the first disk member is a deep-drawn member.

16. The massage device according to claim 12, wherein the collar projects from the inner surface of the first disk member.

17. The massage device according to claim 1, wherein each rolling body comprises three disk members, the disk members being flat bevel wheels and each disk member having one of the rows of projections.

* * * * *